US009888857B2

(12) United States Patent
Samadani et al.

(10) Patent No.: US 9,888,857 B2
(45) Date of Patent: Feb. 13, 2018

(54) METHODS AND SYSTEMS FOR REDUCING ENERGY CONSUMPTION OF A HEART RATE MONITOR

(71) Applicant: Qualcomm Incorporated, San Diego, CA (US)

(72) Inventors: Ramin Samadani, Menlo Park, CA (US); Radu Pitigoi-Aron, San Jose, CA (US); Justin Patrick McGloin, Los Altos, CA (US)

(73) Assignee: QUALCOMM Incorporated, San Diego, CA (US)

( * ) Notice: Subject to any disclaimer, the term of this patent is extended or adjusted under 35 U.S.C. 154(b) by 692 days.

(21) Appl. No.: 14/332,918

(22) Filed: Jul. 16, 2014

(65) Prior Publication Data

US 2016/0015275 A1     Jan. 21, 2016

(51) Int. Cl.
*A61B 5/02*     (2006.01)
*A61B 5/0205*   (2006.01)
(Continued)

(52) U.S. Cl.
CPC ........... *A61B 5/0205* (2013.01); *A61B 5/024* (2013.01); *A61B 5/02438* (2013.01); *A61B 5/1118* (2013.01); *A61B 5/7275* (2013.01); *A61B 5/0022* (2013.01); *A61B 5/02416* (2013.01); *A61B 5/112* (2013.01); *A61B 5/4809* (2013.01); *A61B 5/681* (2013.01); *A61B 2560/0204* (2013.01); *A61B 2562/0219* (2013.01)

(58) Field of Classification Search
CPC ..................................................... A61B 5/021
See application file for complete search history.

(56) References Cited

U.S. PATENT DOCUMENTS 5,749,366 A    5/1998  Odagiri et al.
5,853,364 A *  12/1998 Baker, Jr. ........... A61B 5/02416
                                                  367/155
(Continued)

FOREIGN PATENT DOCUMENTS

WO    2013038296 A1    3/2013

OTHER PUBLICATIONS

Written Opinion—PCT/US2015/035159—ISA/EPO—dated Jul. 25, 2016.
International Search Report and Written Opinion—PCT/US2015/035159—ISA/EPO—dated Dec. 18, 2015.

*Primary Examiner* — Patricia Mallari
*Assistant Examiner* — Vasuda Ramachandran
(74) *Attorney, Agent, or Firm* — Blakely, Sokoloff, Taylor & Zafman

(57) ABSTRACT

Disclosed is an apparatus and method for automatically configuring a mobile device for collecting and inferring heart rate data of a user. The method may include capturing heart rate data for a user with a heart rate sensor that is coupled with a mobile device. The method may also include monitoring a activity state of the user from activity data captured by the mobile device, and detecting a constant activity state of the user. The method may also include inferring heart rate data for the user from the captured heart rate data during a period in which the user remains in the constant activity state. The method may also include providing the inferred heart rate data, as captured heart rate data, to a heart rate calculator during the period in which the user remains in the constant activity state.

27 Claims, 4 Drawing Sheets

(51) Int. Cl.
   *A61B 5/024*   (2006.01)
   *A61B 5/11*    (2006.01)
   *A61B 5/00*    (2006.01)

(56) References Cited

U.S. PATENT DOCUMENTS

| | | |
|---|---|---|
| 8,360,904 B2 | 1/2013 | Oleson et al. |
| 2010/0033422 A1* | 2/2010 | Mucignat ............ G06F 1/1626 |
| | | 345/156 |
| 2012/0317430 A1 | 12/2012 | Rahman et al. |
| 2013/0124891 A1 | 5/2013 | Donaldson |
| 2013/0158686 A1 | 6/2013 | Zhang et al. |
| 2014/0073486 A1 | 3/2014 | Ahmed et al. |
| 2014/0135612 A1* | 5/2014 | Yuen ................ A61B 5/02405 |
| | | 600/407 |
| 2014/0213858 A1* | 7/2014 | Presura ................ A61B 5/721 |
| | | 600/301 |

\* cited by examiner

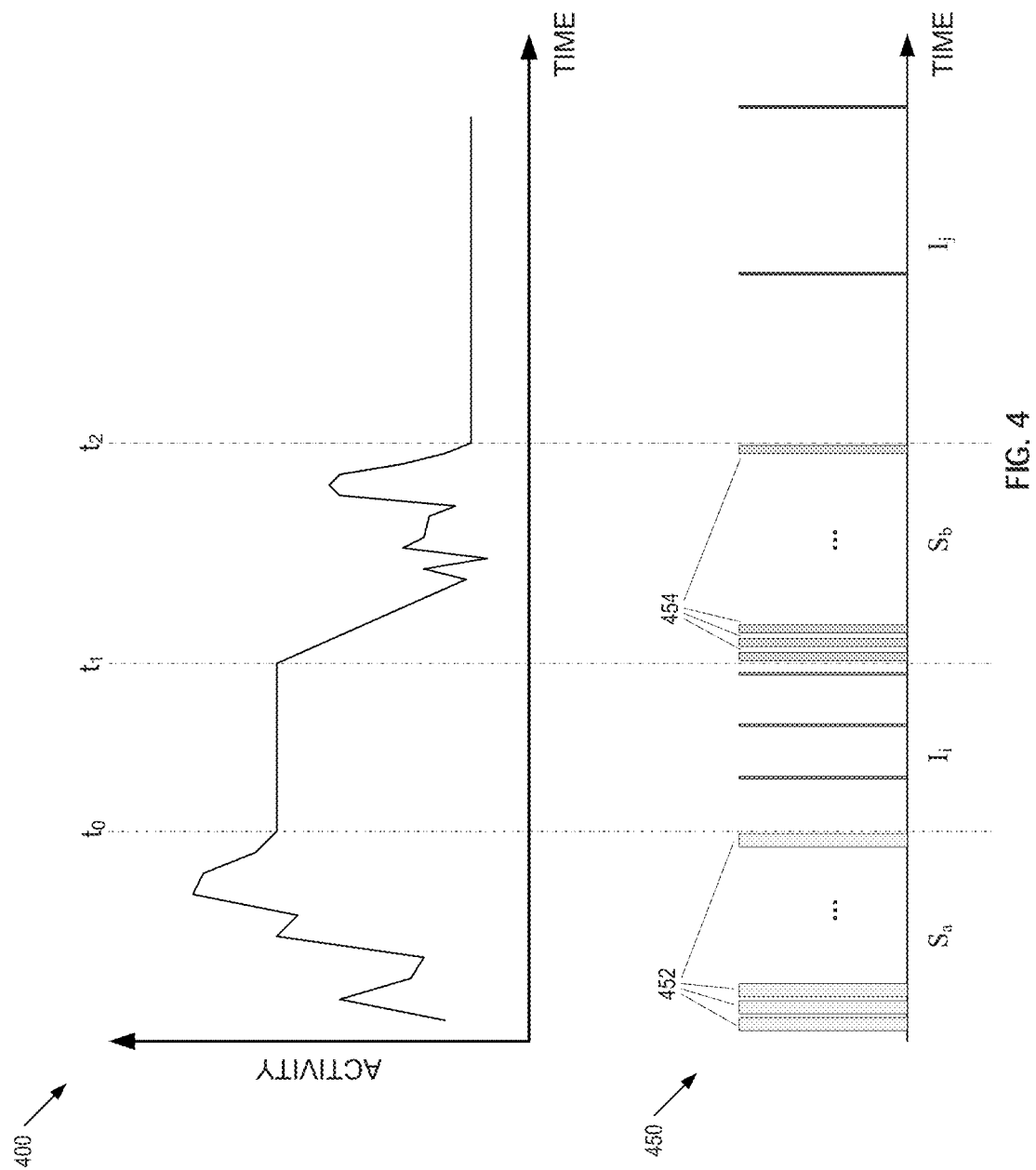

METHODS AND SYSTEMS FOR REDUCING ENERGY CONSUMPTION OF A HEART RATE MONITOR

FIELD

The subject matter disclosed herein relates generally to configuring a mobile device for energy efficient heart rate data collection.

BACKGROUND

The ability to determine a user's heart rate is valuable for many fitness applications, including meeting heart rate targets, calculating recovery times, calculating calorie expenditure, etc. Portable and/or wearable heart rate monitors enable the everyday tracking of heart rate. However, the energy consumption required for continuous and/or repetitive heart rate measurement is very high. The problem becomes exacerbated when heart rate measurement is performed with mobile (e.g., portable, handheld, wearable, etc. devices), which have a limited power supply.

To address energy consumption issues, some approaches for reducing energy consumption of heart rate monitors include lowering the duty cycle of the pulses associated with LED light sources. The energy consumption remains high because continuous heart rate monitoring is performed. Thus, continuous heart rate monitoring on a mobile device would leave little energy for other uses.

BRIEF DESCRIPTION OF THE DRAWINGS

FIG. 4 illustrates one embodiment of the utilization of different sampling and heart rate inference protocols based on monitored user activity levels.

DETAILED DESCRIPTION

Figure 1:
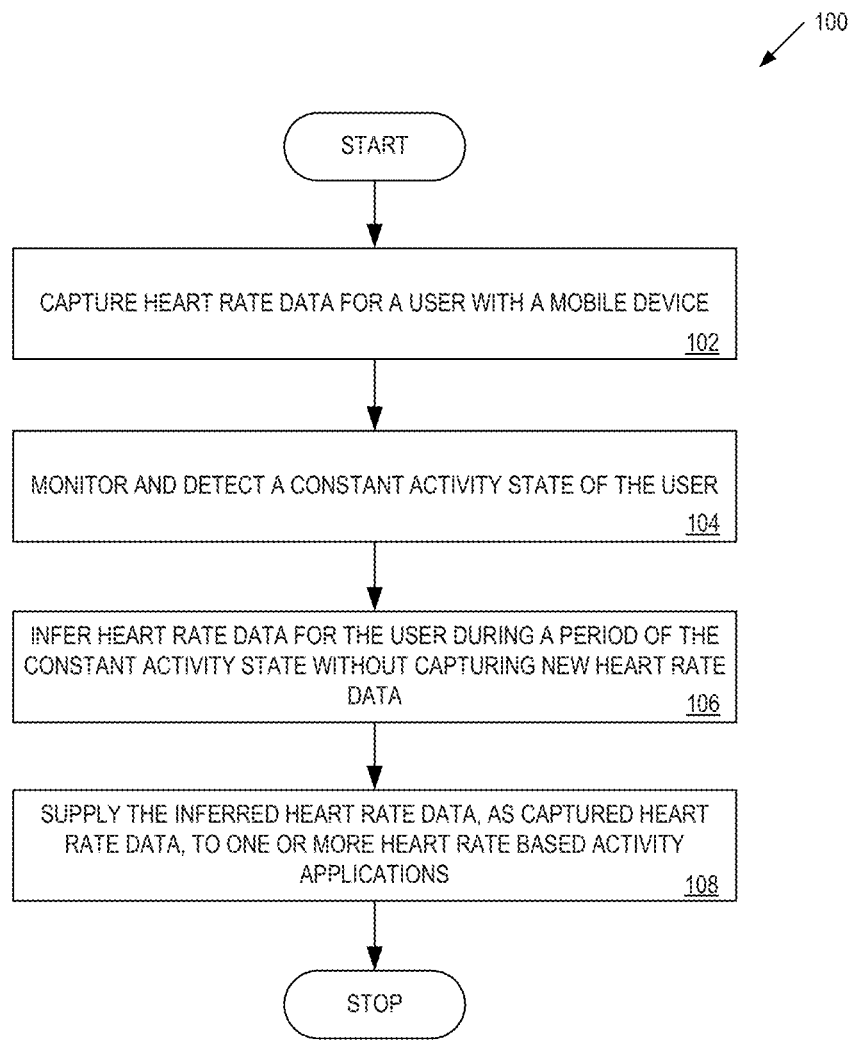
FIG. 1 is a flow diagram of one embodiment of a method for the energy efficient collection of heart rate data.

Methods and systems are disclosed herein for automatically configuring a mobile device for collecting and inferring heart rate data of a user. In one embodiment, the mobile device may be a wearable device, such as a fitness tracking wristband, smartwatch, activity tracker, or other wearable device. Furthermore, mobile devices, such as mobile telephones, tablet computers, etc. which are capable of collecting heart rate data from a user, or which are communicatively coupled with a portable heart rate data collection device, may also be utilized to collect and infer user heart rate data, as discussed herein. For ease of discussion, the remaining description will utilize the terms wearable device and mobile device interchangeably, and not by way of limitation.

In one embodiment, heart rate data collection by a wearable device is controlled based on a user's activity. In one embodiment, the wearable device includes a heart rate sensor, such as an optical heart rate sensor. However, other types of heart rate sensors may be utilized instead of, or in combination with the optical heart rate sensor, by the methods and systems discussed herein. In order to utilize activity-based controls for heart rate data collection, an activity monitor is employed to periodically measure the user's activity. The user activity may be monitored with data collected from one or more activity sensors, such as accelerometers, of the wearable device. The user's activity data may then be analyzed to determine the user's current activity level and/or activity type. For example, the user's activity may be classified according to a plurality of levels, such may be inactive, light activity, high activity, etc. As another example, the user's activity may be classified according to types of activity, such as sleeping, walking, running, etc.

Based on the determined activity classification of a user, in one embodiment, a sampling protocol may be selected. The sampling protocol defines a sampling rate of a heart rate monitor, a collection time period during which heart rate is collected, a time interval between collection time periods, etc. The heart rate monitor then collects heart rate data based on the selected sampling protocol. In one embodiment, as the user's activity changes, as determined from the activity sensors and activity classification, the sampling protocol may be automatically changed or adjusted.

In one embodiment, when the user's determined activity type over a period of time predetermines a more or less constant heart rate, a sampling protocol is selected that reduces the sampling rate, reduces collection time period, and increases time between collection periods of the heart rate monitor based on the determined user activity level and/or classification. Conversely, as the user's determined activity type predetermines a variable heart rate, a sampling protocol is selected that increases the sampling rate, increases the collection time period, and/or reduces the time interval between collection time periods of the heart rate monitor to account for the additional data needed to maintain a minimum level of accuracy. For example, it may be determined that a user's activity type has transitioned from highly variable to inactive. Whereas highly variable activities requires a higher sampling rate and frequent sampling periods to maintain accuracy of heart rate data, an inactive or non-variable period requires a greatly reduced sampling rate, period, and collection in order to obtain the same degree of accuracy.

In one embodiment, a user's heart rate is inferred during time periods of constant user activity. That is, during a time of constant user activity, regardless of whether the user's activity is of a high level (i.e., climbing stairs, running, bicycling, etc.) or a low level (i.e., sleeping, sitting, etc.), a constant heart rate can be inferred for the time period of constant activity. For example, when a user is in an inactive state for a period of time, no data need be collected, as a previously determined heart rate is applied during the inactive period. Similarly, in one embodiment, for activities that are classified as being "constant" over a period of time, such as sleeping for a period of time, walking at the same rate for a period of time, etc., a previously obtained heart rate value can be utilized to infer later heart rate values during the time of constant activity, without acquiring new or additional heart rate data. More specifically, when an activity, irrespective of intensity, is determined as being constant for a period of time, then an inferred heart rate can be applied as a current heart rate and provided to a heart rate monitor, fitness tracker, or other applications. In one embodiment, the heart rate monitor, fitness tracker, and/or applications may then use the inferred heart rate as an actual user heart rate when, for example, determining heart-rate based user calorie expenditure.

In one embodiment, during a time period of constant user activity, during which a previously measured heart rate is inferred as the user's current heart rate, a test heart rate sample may be collected to verify that an inferred heart rate corresponds with the user's actual heart rate. In one embodiment, the tested heart rate confirms, within a predetermined degree of error, that the inferred heart rate is correct. The test heart rate sample may include collecting a minimum amount of data, such as largest time periods between test samples, shortest collection time period, etc., which satisfy minimum accuracy requirements. In one embodiment, the configuration parameters for test heart rate sample collection that assure minimum accuracy requirements may be predetermined for types of constant activity for which the user's heart rate is being inferred. In one embodiment, the configuration parameters for test heart rate sample collection may be dynamically generated based on a user's current activity. For example, test heart rate sampling may be performed more frequently when the user's constant activity, for which heart rate is being inferred, is running, as compared to test heart rate sampling when the user's constant activity is sleeping.

In one embodiment, when the character of activity changes from constant to variable, then a new set of heart rate data measurements is taken. In one embodiment, the sampling and heart rate inference protocols may be determined prior to a user actively using the heart rate monitor. The pre-configured sampling protocols may then be selected based on monitored user activity, as discussed above. In another embodiment, sampling and inference protocol factors, such as sampling frequency, length of sample, time between samples, are dynamically adjusted and then tested for accuracy. Based on analysis of the tested factors, the protocol may be further adjusted until a minimum amount of sampling achieves a sufficiently accurate result. The selected, or dynamically adjusted, sampling protocols may then be implemented in response to current variable and constant monitored user activity levels and/or types. The selected sampling protocol and/or protocol factors enables the heart rate monitor to collect an amount of heart rate data sufficient to determine a user's heart rate without a significant loss of accuracy. Furthermore, by adjusting the heart rate data collection, the energy consumed by the heart rate monitor is greatly reduced.

FIG. 1 is a flow diagram of one embodiment of a method 100 for the energy efficient collection of heart rate data. The method 100 is performed by processing logic that may comprise hardware (circuitry, dedicated logic, etc.), software (such as is run on a general purpose computer system or a dedicated machine), firmware, or a combination.

Referring to FIG. 1, processing logic begins by capturing heart rate data for a user with a mobile device (processing block 102). In one embodiment, the mobile device may be a wearable device, such a fitness tracking wristband, activity tracker, smartwatch, fitness watch, in-ear headphones, or other wearable device capable of capturing user heart rate data. However, other mobile devices, as discussed above, may be utilized according to the discussion herein. Furthermore, mobile device may be communicably coupled with a remote heart rate monitor.

In one embodiment, the user's heart rate data may be captured according to a default sampling protocol, which defines collection factors, such as frequency of collection periods, length of collection periods, time between collection periods, etc. In another embodiment, the continuous heart rate data collection may be performed according to an activity based sampling protocol, where the collection factors are adjusted based on the type or level of user activity. In either embodiment, processing logic performs continuous heart rate data collection based upon the selected sampling protocol.

In FIG. 4, an example 400 of user activity over a period of time is illustrated. Up until time $t_0$, the user's activity level and/or activity type is variable. In one embodiment, a sampling protocol, $S_a$, may be based on the level of variability in the user's activity, activity level, and/or activity type. In one embodiment, it is assumed that because of the variability in the user's activity up to time $t_0$, the user's heart rate will also be variable. In one embodiment, heart rate data sampling and inference protocols are illustrated 450. As illustrated, the rectangles bars 452 in 450 show collection time periods when user heart rate data is being collected, and the time between 454 the rectangular bars show the time intervals between collection time periods. Furthermore, for each of the illustrated collection periods during $S_a$ and $S_b$, there is a defined signal sampling rate. As illustrated, heart rate data collection is performed according to a first sampling protocol, $S_a$, until time $t_0$. In one embodiment, sampling protocol $S_a$ defines a heart rate sampling frequency, collection time period, and a limited time between collection periods, etc. for which user heart rate data is collected.

Returning to FIG. 1, processing logic then monitors and detects a constant activity state of the user (processing block 104). In one embodiment, the wearable device can include sensors, such as accelerometers, which are utilized to collect data, such as acceleration measurements, indicative of user activity. From the acceleration measurements, processing logic determines when a user is participating in a constant activity type or activity level over a period of time. Examples of constant activity include, but are not limited to, running at a constant pace, bicycling at a constant speed, climbing stairs at a constant rate, descending stairs at a constant rate, walking at a constant pace, doing jumping jacks, sleeping, sitting, etc. As illustrated by the examples, a constant user activity state may include periods of high levels of constant activity, as well as periods of low levels of constant activity. In one embodiment, processing logic monitors and detects the same type and/or level of user activity for a period of time, such as a predetermined threshold amount of time, before determining that the user activity is constant.

In response to detecting a constant activity state of the user, processing logic infers heart rate data for the user during a period of the constant activity state without capturing new heart rate data (processing block 106). In one embodiment, when the user's activity state, such as the user's activity level and/or activity type, remains constant over a period of time, processing logic infers that the user's heart rate will also remain constant over the period of time.

In one embodiment, the capture of new heart rate data is stopped after a period of time in which the inferred heart rate is tested against a sampled heart rate during the period of constant user activity. That is, user heart rate data is sampled for a brief period of time at the beginning of the period of constant user activity in order to verify that the inferred heart rate matches the user's actual heart rate. In one embodiment, there is a match when, for example, the inferred heart rate and the sampled heart rates are within a predetermined margin of error of one another. When the samples match the inferred heart rate over the period of time, the user's heart rate can be determined to be constant. In this embodiment, a sampling protocol can be adaptive to sample frequently at the beginning of a constant activity state (e.g., running) for a period of time until it can be determined that that the user's heart rate will be close to constant. Then after the constancy of the user's heart rate is confirmed, the capture of new heart rate data can be stopped.

In one embodiment, processing logic supplies the inferred heart rate data, as captured heart rate data, to one or more heart rate based applications (processing block 108). In one embodiment, the applications can include fitness tracking applications, sleep quality applications, calorie tracking applications, as well as other applications that utilize user heart rate data.

Based on the inference of processing logic in processing block 106, during a period in which a user is in a constant activity state, processing logic needs not collect new heart rate data. Rather, processing logic utilizes the previously collected heart rate data, which was collected at the beginning of the period of constant user activity, as a current heart. In one embodiment, the pervious heart rate is supplied as the current heart rate until the period of constant user activity stops. During the period in which user heart rate is inferred, the mobile device reduces power consumption by avoiding use of a heart rate sensor to collect heart rate data.

In FIG. 4, the user's activity level and/or type is constant between times $t_0$ and $t_1$. In embodiments discussed herein, heart rate data collected at time $t_0$, may be inferred as the user's current heart rate until time $t_1$ without collecting additional and/or new heart rate data. In another embodiment, once a user is determined as being in a constant activity state, a heart rate may be determined during the constant activity state, and be inferred as the user's heart rate during the constant activity state. Thus, the wearable device performing the heart rate data collection and monitoring may realize power savings during this period of constant user activity since a high power sampling protocol, such as sampling protocol $S_a$ which activates and uses a heart rate sensor, may be avoided. In one embodiment, the user's heart rate is inferred until the user's activity state becomes variable once again, such as at time $t_1$.

Figure 2:
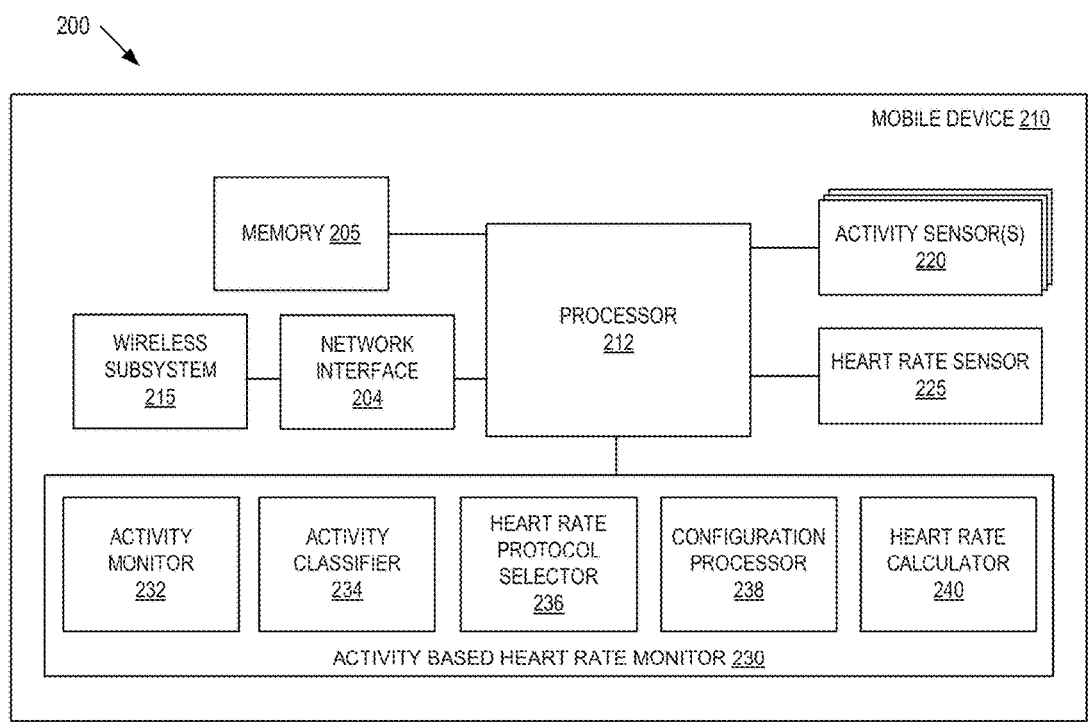
FIG. 2 is block diagram of one embodiment of a mobile device for capturing heart rate data.

FIG. 2 is block diagram of one embodiment 200 of a mobile device 210 for capturing user's heart rate data. In one embodiment, mobile device 210 is a wearable device. In another embodiment, mobile device 210 is a system, such as a mobile telephone. In either embodiment, mobile device 210 may include one or more processors 212, a memory 205, heart rate sensor 225, one or more activity sensor(s) 220, network interface 204.

Mobile device 210 may also include a number of processing modules, which may be implemented as hardware, software, firmware, or a combination, such as the activity monitor 232, activity classifier 234, heart rate protocol selector 236, configuration processor 238, and heart rate calculator 240. It should be appreciated that mobile device 210 may also include, although not illustrated, a power device (e.g., a battery), a display, an audio input and audio output, as well as other components typically associated with wearable or mobile devices. Network interface 204 may also be coupled to a number of wireless subsystems 215 (e.g., Bluetooth, WiFi, Cellular, or other networks) to transmit and receive data streams through a wireless link.

In one embodiment, memory 205 may be coupled to processor 212 to store instructions for execution by the processor 212. In some embodiments, memory 205 is non-transitory. Memory 205 may store activity based heart rate monitor 230, including the processing module listed above, to implement embodiments for collecting and inferring user's heart rate data, as described herein. It should be appreciated that embodiments of the invention as will be hereinafter described may be implemented through the execution of instructions, for example as stored in memory or other element, by processor 212 of mobile device 210, and/or other circuitry of mobile device 210. Particularly, circuitry of mobile device 210, including but not limited to processor 212, may operate under the control of a program, routine, or the execution of instructions to execute methods or processes in accordance with embodiments of the invention. For example, such a program may be implemented in firmware or software (e.g. stored in memory 205) and may be implemented by processors, such as processor 212, and/or other circuitry. Further, it should be appreciated that the terms processor, microprocessor, circuitry, controller, etc., may refer to any type of logic or circuitry capable of executing logic, commands, instructions, software, firmware, functionality and the like.

In one embodiment, a heart rate calculator 240 is responsible for calculating a user's heart rate. In one embodiment, the heart rate may be calculated from heart rate data collected with the heart rate sensor 225. In one embodiment, heart rate sensor 225 is an optical heart rate sensor, although other types of heart rate sensors may be utilized in the system and methods discussed herein. Furthermore, the collection of heart rate data by the heart rate sensor 225 may be controlled by configuration processor 238, which causes heart rate sensor 225 to collect the user's heart rate data according to one of a plurality of different user activity based data collection protocols.

In one embodiment, activity monitor 232 is responsible for monitoring and collecting data from activity sensor(s) 220. In one embodiment, activity sensors include one or more accelerometers, or other motion sensors, that collect data indicative of user activity. In one embodiment, the activity sensor(s) 220 may include multiple types of sensors, may be located at different locations on a user's body, and may be located outside, but coupled to, the mobile device 210. Activity monitor 232 continuously, or periodically, collects data from the activity sensor(s) 220 and provides the data to activity classifier 234.

Activity classifier 234 receives the activity data from the activity monitor 232 and attempts to recognize one or more of a user activity type and a user activity level. The user activity types may include specific real world user activities, such as walking, running, bicycling, sleeping, sitting, etc. The user activity levels may include a differentiation between high, moderate, and low user activity levels. The user activity types and activity levels described herein are exemplary, as other user activity types and levels may be utilized in a manner consistent with the discussion herein. In one embodiment, the activity classifier 234 analyzes the activity data received from the activity sensor(s) 220 to distinguish between activity signatures for different types of user activities, to recognize a level of activity based on a magnitude, frequency, or variability in activity data, as well as to determine user activity from other factors.

Heart rate protocol selector 236 receives the determined user activity type and/or level, and selects a heart rate data collection protocol based on the determined user activity. As discussed herein, the heart rate data collection protocol defines collection period length, frequency of collection periods, time between collection periods, etc. for activating heart rate sensor 225. In one embodiment, the heart rate data collection protocols correspond to the various user activity levels and/or activity types, such that the more active and/or variable a user's activity, the more frequently heart rate data is collected according to the selected collection protocol. The selected heart rate protocol is then provided to configuration processor 238, which as discussed above, controls heart rate sensor's 225 operation for collecting and sampling user's heart rate data.

In one embodiment, activity classifier 234 is further responsible for detecting periods of constant user activity states based on the activity data received from activity monitor 232. In one embodiment, activity classifier 234 detects the same activity level and/or same activity type over a period of time. In one embodiment, when the detected user activity level and/or type remains the same for a predetermined threshold amount of time, activity classifier 234 notifies heart rate protocol selector 236 as to the constant user activity type/level.

Heart rate protocol selector 236 then selects a heart rate inference protocol. In one embodiment, the heart rate inference protocol informs the configuration processor 238 to stop a current heart rate collection protocol, and to provide a prior heart rate data sample to heart rate calculator 240 as current user's heart rate data. In one embodiment, configuration processor 238 continues to provide the prior heart rate data sample to heart rate calculator 240 until activity classifier 234 detects a user activity classification or activity level that conflicts with the previously detected constant user activity. In this instance, the newly detected user activity type and/or activity level are used by heart rate protocol selector 236 to select a data collection protocol for controlling heart rate sensor 225.

In one embodiment, the heart rate inference protocol selected by heart rate protocol selector 236 may also include an optional test sampling protocol. The test sampling protocol defines a brief collection period for collecting user heart rate data to test against the inferred heart rate. FIG. 4 illustrates brief test sampling protocols during periods Ii and Ij in plot 450. In one embodiment, the collection period duration and frequency are determined by heart rate protocol selector 236 based on the determined type and/or level of constant user activity. For example, the duration and/or frequency of test sampling of a user's heart rate may be much less when a user is sleeping as compared to when the user is running. In one embodiment, the collection period defined by the test sampling protocol includes greatly reduced collection frequency, duration, etc. when compared to heart rate data collection when a user's activity is variable, and is utilized by heart rate protocol selector 236 to ensure that the inferred heart rate remains the correct heart rate. Furthermore, in one embodiment, the test sample is not provided to the heart rate calculator 240 as the user's current heart rate, as the heart rate calculator 240 continues to utilize the inferred user heart rate as the user's current heart rate. However, in another embodiment, the heart rate obtained from the test sample may be provided to the heart rate calculator 240 for use as the current user heart rate, or to adjust an inferred heart rate.

As discussed herein, heart rate calculator 240 receives and collects heart rate data for a user of mobile device 210 during periods of variable user activity, and receives inferred heart rate data for the user during periods of constant user activity. In one embodiment, heart rate calculator 240 may utilize the received heart rate data to generate a display for the user, such as a graphical representation of the user's heart rate over a period of time. Heart rate calculator 240 may also provide the calculated heart rate data to one or more fitness applications, such as fitness monitors, calorie trackers, medical applications, etc. which may utilize the user's heart rate within the applications.

In the embodiments discussed herein, mobile device 210 is able to realize significant power saving by utilizing inferred heart rate data during periods of constant user activity. The inferred heart rate enables the activity based heart rate monitor 230 to determine periods of time when not to collect user's heart rate with heart rate sensor 225. However, the inferred heart rate data is still provided to heart rate calculator 240 and/or fitness applications, without the need to supply power to heart rate sensor 225.

Although the heart rate sensor 225, activity sensor(s) 220, activity based hear rate monitor 230, and processor 212 are illustrated as being included in a single device, in one embodiment, the sensors, processing modules, and processing hardware may be distributed among two or more devices. In this embodiment, a combination of sensors (e.g., one or more of sensors 225 and 220) and/or local processing are performed by a first device to pre-process or partially process the user heart rate and/or activity state data as discussed herein. The pre-processed or partially processed data may then be transferred to a second, more computationally powerful device with greater resources, to complete the processing of heart rate and activity state data. The heart rate and/or activity determination results made by the second device, may thereafter be utilized to adjust data collection protocols at the mobile device. For example, a wearable device with one or more heart rate and/or activity sensors may be responsible for collecting heart rate and activity data. The wearable device could then transfer the collected data to a second device (e.g., a mobile telephone, tablet computer, etc.) to complete the processing of activity classification data, activity categorization data, protocol selection, etc. Based on these determinations, the second device could thereafter adjust the heart rate data and activity sensor data collection protocols on the wearable device, as discussed herein.

Figure 3:
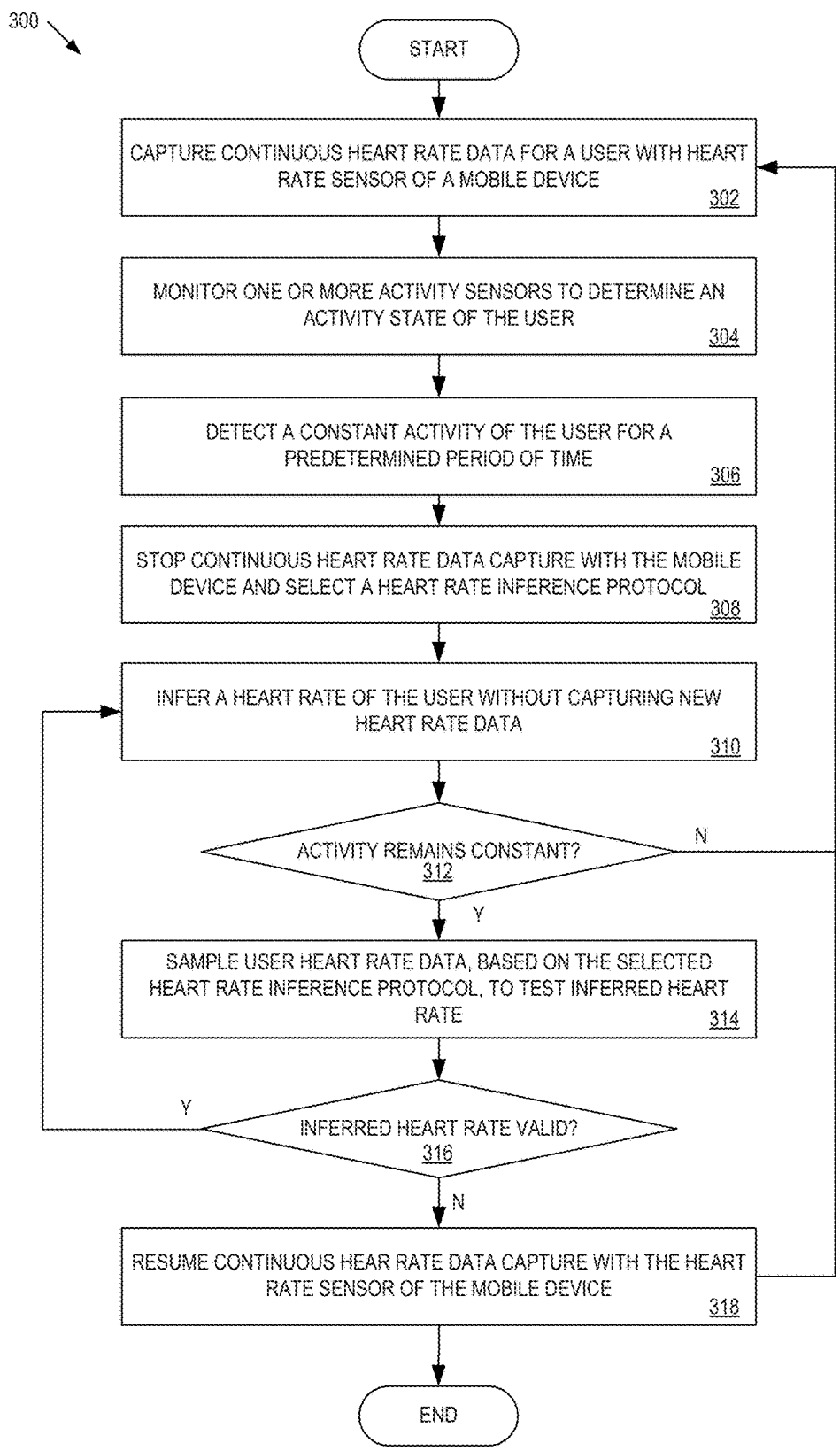
FIG. 3 is a flow diagram of one embodiment for configuring a mobile device to infer user heart rate during periods of constant user activity.

FIG. 3 is a flow diagram of one embodiment of a method 300 for configuring a mobile device to infer user heart rate during periods of constant user activity. The method 300 is performed by processing logic that may comprise hardware (circuitry, dedicated logic, etc.), software (such as is run on a general purpose computer system or a dedicated machine), firmware, or a combination. In one embodiment, the method 300 is performed by a mobile device (e.g., mobile device 210).

Referring to FIG. 3, processing logic begins by capturing continuous heart rate data for a user with a heart rate sensor of a mobile device (processing block 302). In one embodiment, the continuous heart rate data capture may be performed with a user activity based collection protocol. Processing logic monitors one or more activity sensors to determine an activity state of the user (processing block 304). In one embodiment, the determined activity state may include a type of user activity, such as walking, running, sleeping, etc. The determined activity state may also include a level of user activity, such as high, moderate, low, and no user activity. In one embodiment, the determined activity state may include both a determined type and level of user activity, such as highly active running, moderate walking, etc. In one embodiment, the activity state of the user is determined on a periodic or continuous basis.

Processing logic then detects a constant activity state of the user for a predetermined period of time (processing block 306). As discussed herein, the constant activity state may include a period of constant high activity, a period of constant moderate activity, a period of constant inactivity, etc. In response to the detection of the constant activity state, processing logic stops the continuous heart rate data capture and selects a heart rate inference protocol (processing block 308). The user heart rate is thereafter inferred by processing logic without capturing new heart rate data (processing block 310).

As illustrated in FIG. 4, the collection protocol $S_a$ is selected for the period of variable user activity. As illustrated, heart rate data is collected up to time period $t_0$ using protocol $S_a$. In one embodiment, protocol $S_a$ may be selected based on one or more of the variability in user activity, type of user activity, level of user activity, etc. during the corresponding time period. It should be noted that multiple collection protocols could be employed, and dynamically selected according to a current user activity. Furthermore, collection protocols may be adjusted incrementally in a manner that corresponds with changes in user activity.

At time $t_0$, the user's activity level and/or type transitions to a constant activity state. In accordance with the discussion in FIG. 3, a heart rate inference protocol $I_i$ may then be selected. The heart rate inference protocol enables the collection of user heart rate data to be stopped for the duration in which the constant activity state of the user is maintained.

Returning to FIG. 3, processing logic determines whether the activity state of the user remains constant (processing block 312). For example, processing logic determines whether a user continues to run at the same pace, continues to ascend stares at the same rate, continues to sleep, continues to sit, etc. When there is a change in the use's activity state (processing block 312), the process returns to processing block 302 to resume continuous heart rate data capture. However, during the duration of constant user activity, processing logic samples user heart rate data, based on the selected heart rate inference protocol, to test an inferred heart rate (processing block 314). When the inferred heart rate is valid, based on the sample, processing logic returns to processing block 310 to continue inferring the user's heart rate. However, when the inferred heart rate is invalid, such that the sampled test heart rate is outside a threshold beats per minute, threshold percentage, etc., processing logic resumes continuous heart rate data capture (processing block 318).

In one embodiment, the heart rate data sampling for testing validity of an inferred heart rate is performed less often than the heart rate is inferred. That is, a user's heart rate may be inferred every 1 second, 0.5 seconds, etc. during a period of constant user activity. However, the test sampling may occur on a less frequent basis, such obtaining a test sampling of a user's heart rate every minute, every five minutes, etc. In one embodiment, the time between collection of test samples may be based on a type and/or level of constant user activity.

As illustrated in FIG. 4, the heart rate inference protocol may include the periodic collection of heart rate test samples for testing the continued validity of the inferred heart rate. As discussed above, the collection of test samples may be based on the type of constant user activity during time $t_0$ to time $t_1$. When test samples are collected, the sample duration and frequency are much smaller than during heart rate data collection, and the time between test samples is far greater than the time between sampling/collection periods.

Furthermore, at time $t_1$, the user's activity transitions to a variable state, and another heart rate data collection protocol $S_b$ is selected. In one embodiment, the heart rate data collection protocol $S_b$ may be different from collection protocol $S_a$ as a result of different variability of user activity. Again, at time $t_2$, a constant use activity state is detected, and a new heart rate inference protocol $I_j$ is selected. The new heart rate inference protocol $I_j$ may differ from inference protocol $I_i$ based on the determined type and/or level of constant user activity. Based on the determined type of constant user activity, the inference protocol may define less test sampling when, for example, the constant user activity is low versus high, inactive versus active, sleeping versus running, etc.

It should be appreciated that the wearable devices or mobile devices discussed herein may communicate via one or more wireless communication links through a wireless network that are based on or otherwise support any suitable wireless communication technology. For example, in some aspects wearable devices or mobile devices may associate with a network including a wireless network. In some aspects the network may comprise a body area network or a personal area network (e.g., an ultra-wideband network). In some aspects the network may comprise a local area network or a wide area network. A wireless device may support or otherwise use one or more of a variety of wireless communication technologies, protocols, or standards such as, for example, CDMA, TDMA, OFDM, OFDMA, WiMAX, and Wi-Fi. Similarly, a wireless device may support or otherwise use one or more of a variety of corresponding modulation or multiplexing schemes. A mobile or wearable device may wirelessly communicate with other mobile devices, cell phones, other wired and wireless computers, Internet web-sites, etc.

The teachings herein may be incorporated into (e.g., implemented within or performed by) a variety of apparatuses (e.g., devices). For example, one or more aspects taught herein may be incorporated into a wearable device, phone (e.g., a cellular phone), a personal data assistant (PDA), a tablet, a mobile computer, a laptop computer, a tablet, a headset (e.g., headphones, an earpiece, etc.), a medical device, or any other suitable device.

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

In one or more exemplary embodiments, the functions described may be implemented in hardware, software, firmware, or any combination thereof. If implemented in software as a computer program product, the functions may be stored on or transmitted over as one or more instructions or code on a non-transitory computer-readable medium. Computer-readable media can include both computer storage media and communication media including any medium that facilitates transfer of a computer program from one place to another. A storage media may be any available media that can be accessed by a computer. By way of example, and not limitation, such non-transitory computer-readable media can comprise RAM, ROM, EEPROM, magnetic disk storage or other magnetic storage devices, or any other medium that can be used to carry or store desired program code in the form of instructions or data structures and that can be accessed by a computer. Also, any connection is properly termed a computer-readable medium. For example, if the software is transmitted from a web site, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Combinations of the above should also be included within the scope of non-transitory computer-readable media.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A method, comprising:
    capturing, using a heart rate sensor, heart rate data from a user, where the heart rate sensor is coupled with a mobile device;
    providing the heart rate data to a heart rate calculator for determining a heart rate of the user;
    monitoring an activity state of the user from activity data captured by the mobile device; and
    detecting, using a processor, a constant activity state of the user based on the captured activity data; wherein, when the constant activity state is detected;
    stopping, using the processor, the capture of new heart rate data during a period in which the user remains in the constant activity state,
    inferring, using the processor, heart rate data for the user from the captured heart rate data during the period in which the user remains in the constant activity state regardless of an activity level of the user,
    providing, using the processor, the inferred heart rate data to the heart rate calculator, and
    determining, using the heart rate calculator, the heart rate of the user based on the inferred heart rate data during the period in which the user remains in the constant activity state.

2. The method of claim 1, further comprising:
    sampling heart rate data for the user for a period of time after the constant activity state is detected and prior to stopping the capture of new heart rate data;
    determining that the inferred heart rate data during the period of time after the constant activity state is detected matches the sampled heart rate data; and
    stopping the capture of new heart rate data by the heart rate sensor for providing to the heart rate calculator in response to the determining the match;
    wherein the period of time after the constant activity state is detected and prior to stopping the capture of new heart rate data is less than the period of time in which the user remains in the constant activity state.

3. The method of claim 1, further comprising:
    in response to detection of the constant activity state of the user, selecting a heart rate inference protocol based on the constant activity state of the user; and
    inferring heart rate data for the user based on the selected heart rate inference protocol.

4. The method of claim 3, further comprising:
    collecting one or more test heart rate data samples for the user with the heart rate sensor of a mobile device, wherein the one or more test heart rate data samples are collected based on the heart rate inference protocol, and wherein the heart rate inference protocol defines, based on the constant activity state, one or more of a collection period, sample frequency, and time between samples for collection of the one or more test heart rate data samples; and
    resuming the capture of heart rate data for the user by the heart rate sensor for providing to the heart rate calculator when the inferred heart rate data does not correspond with the one or more test heart rate data samples.

5. The method of claim 1, wherein capturing heart rate data for the user comprises:
    selecting a continuous heart rate data capture collection protocol based on the monitored user activity; and
    performing continuous heart rate data capture for the user with the mobile device based on the selected continuous heart rate data capture collection protocol.

6. The method of claim 1, wherein the mobile device is a wearable device.

7. The method of claim 1, wherein the heart rate calculator utilizes the inferred heart rate data to provide the heart rate of the user to a fitness application.

8. The method of claim 1, wherein detecting the constant activity state of the user further comprises:
    detecting one of a plurality of different activity states; and determining that user has remained in the detected one of the plurality of different activity states for a threshold period of time.

9. The method of claim 8, wherein the plurality of different activity states comprises a high activity state, a moderate activity state, a low activity state, and an inactivity state.

10. The method of claim 8, wherein the plurality of different activity states comprises a plurality of different types of user activity comprising at least a running activity state, a walking activity state, and a sleeping activity state.

11. The method of claim 1, wherein capturing the heart rate data for the user further comprises:
 capturing the heart rate data for the user based on a sampling protocol, wherein the sampling protocol defines one or more of a collection period, sample frequency, and time between samples;
 adjusting the sampling protocol based on the monitored activity state of the user.

12. The method of claim 11, wherein adjusting the sampling protocol further comprises:
 adjusting one or more of the collection period, sample frequency, and time between samples based on the monitored activity state;
 determining whether a user heart rate determined from the adjusted one or more of the collection period, sample frequency, and time between samples based on the monitored activity is within an accuracy threshold of the user's actual heart rate; and
 continuing to adjust the one or more of the collection period, sample frequency, and time between samples based on the monitored activity state until the determined user heart rate is within the accuracy threshold of the user's actual heart rate.

13. A non-transitory computer readable storage medium including instructions that are executed by a processor, causing the processor to perform a method comprising:
 capturing, using a heart rate sensor, heart rate data from a user, where the heart rate sensor is coupled with a mobile device;
 providing the heart rate data to a heart rate calculator for determining a heart rate of the user;
 monitoring an activity state of the user from activity data captured by the mobile device; and
 detecting a constant activity state of the user based on the captured activity data; wherein, when the constant activity state is detected:
 stopping the capture of new heart rate data during a period in which the user remains in the constant activity state,
 inferring heart rate data for the user from the captured heart rate data during the period in which the user remains in the constant activity state regardless of an activity level of the user,
 providing the inferred heart rate data to the heart rate calculator, and
 determining, using the heart rate calculator, the heart rate of the user based on the inferred heart rate data during the period in which the user remains in the constant activity state.

14. The non-transitory computer readable storage medium of claim 13, further comprising:
 sampling heart rate data for the user for a period of time after the constant activity state is detected and prior to stopping the capture of new heart rate data;
 determining that the inferred heart rate data during the period of time after the constant activity state is detected matches the sampled heart rate data; and
 stopping the capture of new heart rate data by the heart rate sensor for providing to the heart rate calculator in response to the determining the match;
 wherein the period of time after the constant activity state is detected and prior to stopping the capture of new heart rate data is less than the period of time in which the user remains in the constant activity state.

15. The non-transitory computer readable storage medium of claim 13, further comprising:
 in response to detection of the constant activity state of the user, selecting a heart rate inference protocol based on the constant activity state of the user; and
 inferring heart rate data for the user based on the selected heart rate inference protocol.

16. The non-transitory computer readable storage medium of claim 15, further comprising:
 collecting one or more test heart rate data samples for the user with the heart rate sensor of a mobile device, wherein the one or more test heart rate data samples are collected based on the heart rate inference protocol, and wherein the heart rate inference protocol defines, based on the constant activity state, one or more of a collection period, sample frequency, and time between samples for collection of the one or more test heart rate data samples; and
 resuming the capture of heart rate data for the user by the heart rate sensor for providing to the heart rate calculator when the inferred heart rate data does not correspond with the one or more test heart rate data samples.

17. The non-transitory computer readable storage medium of claim 13, wherein capturing heart rate data for the user comprises:
 selecting a continuous heart rate data capture collection protocol based on the monitored user activity; and
 performing continuous heart rate data capture for the user with the mobile device based on the selected continuous heart rate data capture collection protocol.

18. The non-transitory computer readable storage medium of claim 13, wherein the mobile device is a wearable device.

19. The non-transitory computer readable storage medium of claim 13, wherein the heart rate calculator utilizes the inferred heart rate data to provide the heart rate of the user to a fitness application.

20. The non-transitory computer readable storage medium of claim 13, wherein detecting the constant activity state of the user further comprises:
 detecting one of a plurality of different activity states; and
 determining that user has remained in the detected one of the plurality of different activity states for a threshold period of time.

21. The non-transitory computer readable storage medium of claim 20, wherein the plurality of different activity states comprises a high activity state, a moderate activity state, a low activity state, and an inactivity state.

22. The non-transitory computer readable storage medium of claim 20, wherein the plurality of different activity states comprise a plurality of different types of user activity comprising at least a running activity, a walking activity, and a sleeping activity.

23. The non-transitory computer readable storage medium of claim 13, wherein capturing the heart rate data for the user further comprises:
 capturing the heart rate data for the user based on a sampling protocol, wherein the sampling protocol defines one or more of a collection period, sample frequency, and time between samples;

adjusting the sampling protocol based on the monitored activity state of the user.

24. The non-transitory computer readable storage medium of claim 23, wherein adjusting the sampling protocol further comprises:
adjusting one or more of the collection period, sample frequency, and time between samples based on the monitored activity state;
determining whether a user heart rate determined from the adjusted one or more of the collection period, sample frequency, and time between samples based on the monitored activity is within a accuracy threshold of the user's actual heart rate; and
continuing to adjust the one or more of the collection period, sample frequency, and time between samples based on the monitored activity state until the determined user heart rate is within the accuracy threshold of the user's actual heart rate.

25. A mobile device, comprising:
an activity sensor;
a heart rate sensor; and
a processor coupled with the activity sensor and the heart rate sensor, wherein the processor is configured to
capture heart rate data from a user with the heart rate sensor,
provide the heart rate data to a heart rate calculator for determining a heart rate of the user,
monitor an activity state of the user from activity data captured by the activity sensor,
detect a constant activity state of the user based on the captured activity data, wherein, when the constant activity state is detected, the processor is further configured to
stop the capture of new heart rate data during a period in which the user remains in the constant activity state,
infer heart rate data for the user from the captured heart rate data during the period in which the user remains in the constant activity state regardless of an activity level of the user, and
provide the inferred heart rate data to the heart rate calculator, and
determine the heart rate of the user based on the inferred heart rate data during the period in which the user remains in the constant activity state.

26. The mobile device of claim 25, further comprises the processor configured to
in response to detection of the constant activity state of the user, select a heart rate inference protocol based on the constant activity state of the user, and
infer heart rate data for the user based on the selected heart rate inference protocol.

27. A system comprising:
means for capturing heart rate data from a user with a heart rate sensor that is coupled with a mobile device;
means for providing the heart rate data to a heart rate calculator for determining a heart rate of the user;
means for monitoring an activity state of the user from activity data captured by the mobile device;
means for detecting a constant activity state of the user based on the captured activity data,
means for stopping the capture of new heart rate data during a period in which the user remains in the constant activity state;
means for inferring heart rate data for the user from the captured heart rate data during the period in which the user remains in the constant activity state regardless of an activity level of the user; and
means for providing the inferred heart rate data, to the heart rate calculator for determining the heart rate of the user based on the inferred heart rate data during the period in which the user remains in the constant activity state.

* * * * *